(12) United States Patent
Nicholas et al.

(10) Patent No.: US 9,908,824 B2
(45) Date of Patent: Mar. 6, 2018

(54) METHODS FOR SELECTIVELY HYDROGENATING BENZENE WITH SUPPORTED ORGANOMETALLIC CATALYSTS AND SYSTEMS AND METHODS FOR REDUCING BENZENE IN GASOLINE USING SUCH CATALYSTS

(71) Applicant: UOP LLC, Des Plaines, IL (US)

(72) Inventors: Christopher P. Nicholas, Evanston, IL (US); Massimiliano Delferro, Chicago, IL (US); Weixing Gu, Shanghai (CN); Tobin Jay Marks, Evanston, IL (US); Alakananda Bhattacharyya, Glen Ellyn, IL (US)

(73) Assignees: UOP LLC, Des Plaines, IL (US); Northwestern University, Evanston, IL (US)

( * ) Notice: Subject to any disclaimer, the term of this patent is extended or adjusted under 35 U.S.C. 154(b) by 128 days.

(21) Appl. No.: 14/167,603

(22) Filed: Jan. 29, 2014

(65) Prior Publication Data

US 2015/0210612 A1     Jul. 30, 2015

(51) Int. Cl.
*C07C 5/10* (2006.01)
*C10G 45/46* (2006.01)

(52) U.S. Cl.
CPC .............. *C07C 5/10* (2013.01); *C10G 45/46* (2013.01); *C07C 2521/04* (2013.01);
(Continued)

(58) Field of Classification Search
CPC ............ C07C 5/10; C07C 7/163; C10G 45/46
(Continued)

(56) References Cited

U.S. PATENT DOCUMENTS

| 4,514,337 A | 4/1985 | Pez |
| 4,731,496 A | 3/1988 | Hu et al. |

(Continued)

FOREIGN PATENT DOCUMENTS

| CN | 100497542 C | 6/2009 |
| CN | 102600888 A | 7/2012 |

(Continued)

OTHER PUBLICATIONS

Diehl, J.W.; Finkbeiner, J.W.; DiSanzo, F.P. "Determination of Benzene, Toluene, Ethylbenzene, and Xylenes in Gasolines by Gas Chromatography/Deuterium Isotope Dilution Fourier Transform Infrared Spectroscopy", Anal. Chem. (1993), 65, pp. 2493-2496.*

(Continued)

*Primary Examiner* — In Suk Bullock
*Assistant Examiner* — Aaron Pierpont

(57) ABSTRACT

Methods and systems for selectively hydrogenating benzene with a supported organometallic hydrogenating catalyst are provided. An exemplary method includes contacting an arene-containing reaction stream comprising benzene and one or more additional arenes with hydrogen in the presence of a supported organometallic hydrogenating catalyst under reaction conditions effective to hydrogenate at least benzene in the arene-containing reaction stream to produce a reaction effluent having a ratio of benzene to additional arenes that is lower than a ratio of benzene to additional arenes in the reaction stream. In this method, the supported organometallic hydrogenating catalyst includes a catalytically active organometallic species and a Brønsted acidic sulfated metal oxide support.

20 Claims, 8 Drawing Sheets

(52) U.S. Cl.
CPC ...... *C07C 2521/06* (2013.01); *C07C 2523/30* (2013.01); *C07C 2527/02* (2013.01); *C07C 2531/22* (2013.01); *C07C 2531/38* (2013.01); *C10G 2400/02* (2013.01)

(58) Field of Classification Search
USPC .......................................... 585/258, 250, 266
See application file for complete search history.

(56) References Cited

U.S. PATENT DOCUMENTS

| | | | |
|---|---|---|---|
| 5,345,026 A | 9/1994 | Chang et al. | |
| 5,424,264 A | 6/1995 | Richard et al. | |
| 5,449,847 A | 9/1995 | Chang et al. | |
| 5,773,670 A | 6/1998 | Gildert et al. | |
| 5,856,602 A | 1/1999 | Gildert et al. | |
| 5,856,607 A * | 1/1999 | Kim ...................... | C07C 15/073 585/314 |
| 6,187,980 B1 | 2/2001 | Gildert | |
| 6,235,918 B1 * | 5/2001 | Marks .................... | B01J 27/053 502/120 |
| 7,790,943 B2 | 9/2010 | Lin et al. | |

FOREIGN PATENT DOCUMENTS

| | | |
|---|---|---|
| CN | 102671659 A | 9/2012 |
| JP | 03742870 B2 | 2/2006 |

OTHER PUBLICATIONS

Kazakov, et al., "Hydroisomerization of Benzene-Containing Gasoline Fractions on A—ZrO2—Al2O3 Catalyst: III. The Hydrogenating Properties of the Catalyst," Kinetics and Catalysis, v 53, n 1, p. 101-106, Feb. 2012.

Kazakov, et al., "Hydroisomerization of Benzene-Containing Gasoline Fractions on a Pt/SO42—ZrO2—Al2O3 Catalyst: II. Effect of Chemical Composition on Acidic and Hydrogenating and the Occurrence of Model Isomerization Reactions," Kinetics and Catalysis, v 52, n 4, p. 573-578, Jul. 2011.

Kazakov, et al., "Hydroisomerization of Benzene-Containing Gasoline Fractions on a Pt/SO42—ZrO2—Al2O3 Catalyst: I. Effect of Chemical Composition on the Phase State and Texture Characteristics of SO42—ZrO2—Al2O3," Supports Kinetics and Catalysis, v 51, n 3, p. 438-443, Jun. 2010.

Ahn, et al., "Surface Organozirconium Electrophiles Activated by Chemisorption on "Super Acidic" Sulfated Zirconia as Hydrogenation and Polymerization Catalysts. A Synthetic, Structural, and Mechanistic Catalytic Study," Department of Chemistry, Northwestern University, Organometallics 2002, 21, 1788-1806, Jan. 27, 2002.

"NPRA Question & Answer Session on Refining and Petrochemical Technology," IV. Light Oil Catalytic Processing, p. 136-164, conducted by the National Petroleum Refiners Association, 1992.

Williams et al., "Synthesis, Characterization, and Heterogeneous Catalytic Implementation of Sulfated Alumina Nanoparticles, Arene Hydrogenation and Olefin Polymerization Properties of Supported Organozirconium Complexes", ACS Catalysis, vol. 1 (4), pp. 238-245, American Chemical Society, Feb. 21, 2011.

Nicholas et al., Synthesis, Spectroscopy, and Catalytic Properties of Cationic Organozirconium Adsorbates on "Super Acidic" Sulfated Alumina. "Single-Site" Heterogeneous Catalysts with Virtually 100% Active Sites. JACS Articles, Journal of American Chemical Society, vol. 125, pp. 4325-4331, American Chemical Society, Mar. 15, 2003.

Herzog et al., "2,4,6-Trimethylpyridine-bishydrofluoride; a novel fluorinating reagent for organo transition-metal alkyls", Chemical Communications, 1996, issue 1, pp. 29-30, Jan. 7, 1996.

Pellecchia et al., Single insertion of propene into a cationic zirconium(IV) complex: isolation and X-ray crystal structure of [(C5Me5,)Zr(CH2CHMeCH2Ph)(CH2h)]-[B(CH2Ph)(C6F5)3], Journal of Organometallic Chemistry, vol. 470, 1994.

* cited by examiner

METHODS FOR SELECTIVELY HYDROGENATING BENZENE WITH SUPPORTED ORGANOMETALLIC CATALYSTS AND SYSTEMS AND METHODS FOR REDUCING BENZENE IN GASOLINE USING SUCH CATALYSTS

GOVERNMENT INTERESTS

This invention was made with government support under grant numbers CHE0923236 and CHE1048773 awarded by the National Science Foundation. The government has certain rights in this invention.

TECHNICAL FIELD

The technical field generally relates to methods of selectively hydrogenating benzene in the presence of other arenes, and more particularly relates to methods for selectively hydrogenating benzene in the presence of other arenes with supported organometallic catalysts and systems and methods for reducing benzene in gasoline products using such catalysts.

BACKGROUND

The ability to selectively hydrogenate benzene in the presence of other arenes has been of interest in the refinery industry due to strict government limitations on the concentration of benzene in gasoline products. In the United States, benzene content is currently limited to an average of 0.62% by volume, while in Europe the limit is marginally higher, at 1%. In a refinery, the highest percentage of benzene in the overall gasoline pool comes from the reforming of naphtha into aromatics. The most frequently utilized method of reducing benzene in the gasoline pool is to prefractionate the naphtha to eliminate the C6 component in the reformer feed and thus the amount of benzene formed. However, this approach reduces the feed available to yield gasoline.

A standard method of removing benzene from gasoline streams such as reformed naphtha is extractive distillation. This method utilizes a solvent with affinity for aromatics such as benzene, distills other compounds overhead and recovers an aromatic containing solvent, which can then be separated. Another commonly used method of removing benzene is liquid-liquid extraction. This method utilizes a solvent with an affinity for aromatic molecules. The solvent and the aromatic containing stream are passed in countercurrent fashion to recover a solvent rich in aromatics which can be separated. These methods are not selective to benzene. That is, these methods also reduce the amounts of aromatic molecules other than benzene that are present in the stream. It would be beneficial to reduce the benzene content without significantly reducing other aromatic molecule content.

Another industrially important technique is the alkylation of benzene with propene to i-propylbenzene (cumene) carried out using zeolites as an acid catalyst. However, this approach requires significant cleanup of impurities in refinery propene, considerably adding to the required capital cost for commercial use of the technique. Further complicating this technique is the fact that that current commercial metal hydrogenation catalysts (e.g., $Pd/Al_2O_3$, $Pt/Al_2O_3$, $Ni/Al_2O_3$) display marginal reactivity differences between hydrogenation of benzene and other substituted arenes, such as toluene, due to preferential adsorption and hydrogenation on the catalytic surface of substituted aromatics. Furthermore, with $Pd/Al_2O_3$ at elevated pressures (e.g., $P_{H2} \geq$ about 40 atm) and temperatures (about 110 to about 160° C.) such as are commonly used, minimal selectivity for benzene is observed. The relative hydrogenation rate over Pd catalyst at an equimolar feed composition of 50% toluene and 50% benzene is 0.65±0.10, with little observed dependence on the particular catalyst support or reaction temperature. Additionally, with increasing overall aromatic conversion, selectivity for benzene hydrogenation diminishes. Thus, special engineering designs are applied in commercial refineries to reduce the loss of toluene during benzene hydrogenation processing. Usually this takes the form of separating benzene from toluene by fractionation and hydrogenating the stream comprising benzene in a separate reactor, such as taught by U.S. Pat. No. 5,003,118. However, this approach increases cost due to the additional reactor.

Accordingly, it is desirable to provide methods for the selective hydrogenation of benzene at least over toluene from a complex reactant stream. In addition, it is desirable to provide systems and methods for the selective removal of benzene from gasoline. Furthermore, other desirable features and characteristics of the present invention will become apparent from the subsequent detailed description and the appended claims, taken in conjunction with the accompanying drawings and this background.

BRIEF SUMMARY

Methods for selectively hydrogenating benzene with a supported organometallic catalyst and methods and systems for reducing benzene in gasoline products using the catalysts are provided herein. In accordance with an exemplary embodiment, a method for selectively hydrogenating benzene with a supported organometallic hydrogenating catalyst includes contacting an arene-containing reaction stream comprising benzene and one or more additional arenes with hydrogen in the presence of a supported organometallic hydrogenating catalyst under reaction conditions effective to hydrogenate at least benzene in the arene-containing reaction stream to produce a reaction effluent having a ratio of benzene to additional arenes that is lower than a ratio of benzene to additional arenes in the reaction stream. In this embodiment, the supported organometallic hydrogenating catalyst comprises a catalytically active organometallic species and a Brønsted acidic sulfated metal oxide support.

In another exemplary embodiment, a method for reducing benzene in a gasoline product includes contacting an arene-containing reaction stream comprising benzene and one or more additional arenes with hydrogen in the presence of a supported organometallic hydrogenating catalyst under reaction conditions effective to hydrogenate benzene in the arene-containing reaction stream to produce an effluent having a ratio of benzene to other arenes in the effluent lower than a ratio of benzene to other arenes in the arene-containing stream. In these embodiments, wherein the arene-containing reaction stream comprises a refinery stream, and the supported organometallic hydrogenating catalyst comprises a catalytically active organometallic species and a Brønsted acidic sulfated metal oxide support.

Also provided herein are systems for reducing benzene in a gasoline product. The systems include a reaction vessel configured to contain a catalytically active organometallic species on a Brønsted acidic sulfated metal oxide support. In these systems, the reaction vessel is configured to receive and contact a refinery stream and hydrogen gas with the supported organometallic catalyst under reaction conditions effective to hydrogenate benzene in the refinery stream to produce an effluent. In these systems, the refinery stream contains benzene and one or more other arenes. In an exemplary embodiment, a ratio of benzene to the one or more arenes in the effluent is lower than a ratio of benzene to the one or more arenes in the refinery stream.

DETAILED DESCRIPTION OF THE DRAWINGS

The various embodiments will hereinafter be described in conjunction with the following drawing figures, wherein like numerals denote like elements, and wherein.

Figure 3A:
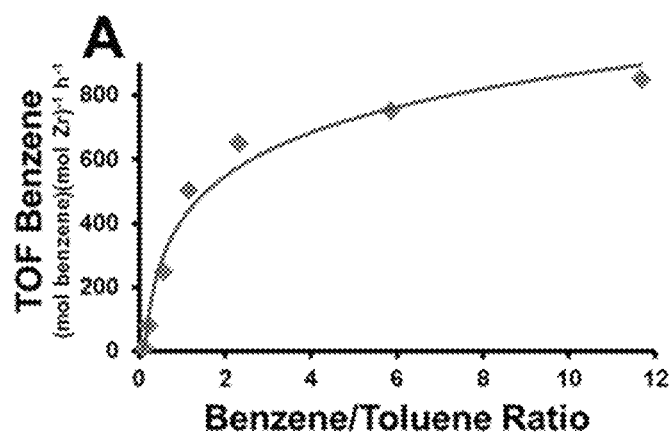
Figure 3A:
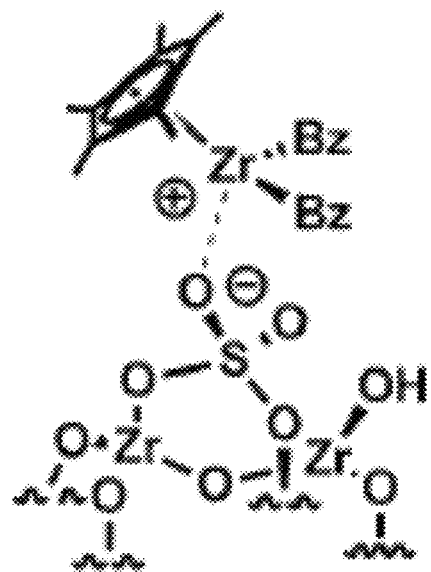
Figure 3B:
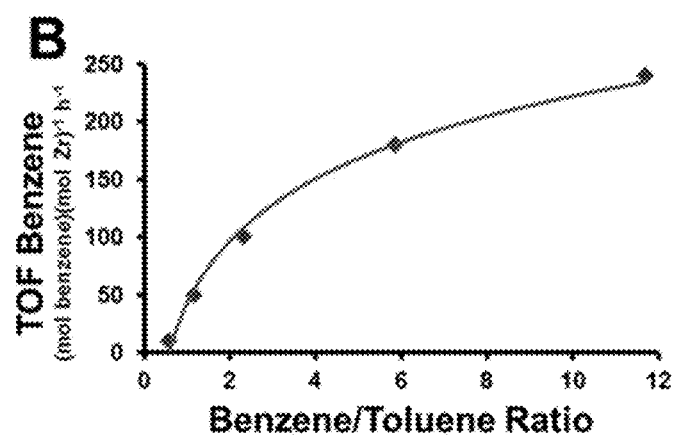
Figure 3B:
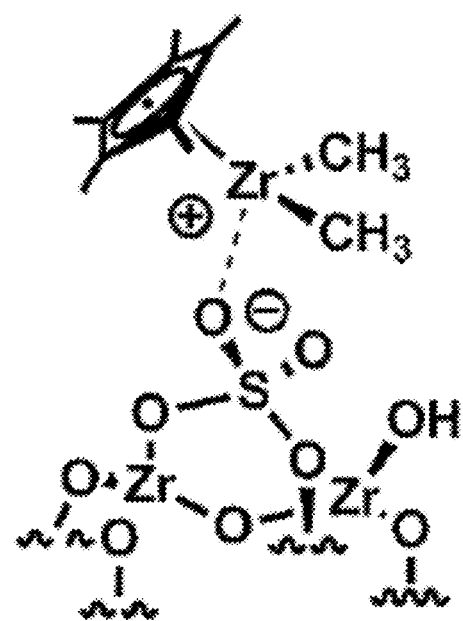
Figure 3C:
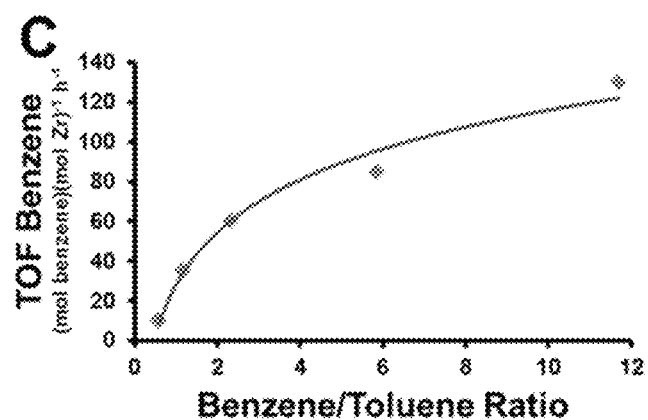
Figure 3C:
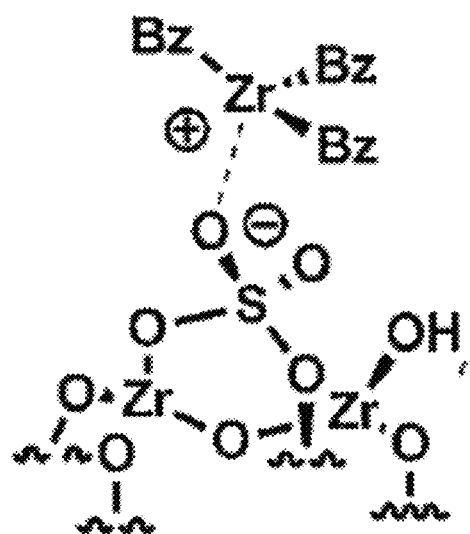
Figure 3D:
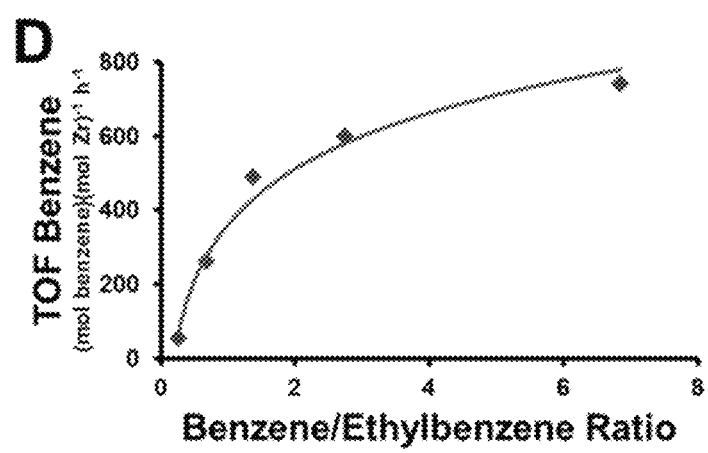
Figure 3E:
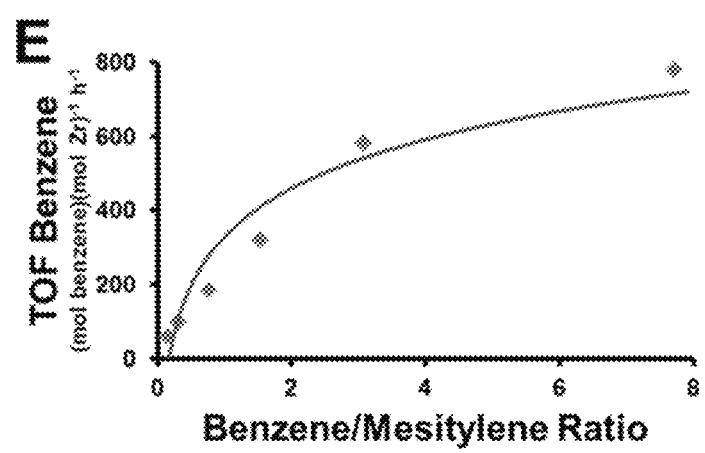

FIG. 3A-E are Michaelis-Menten kinetics plots for competitive inhibition of benzene hydrogenation by various arenes (toluene inhibition with $Cp*ZrBz_2/ZrS$ as the catalyst is shown in FIG. 3A; toluene inhibition with $Cp*ZrMe_2/ZrS$ as the catalyst is shown in FIG. 3B; toluene inhibition with $ZrBz_3/ZrS$ as the catalyst is shown in FIG. 3C; ethylbenzene inhibition with $CpZrBz_2/ZrS$ as the catalyst is shown in FIG. 3D; mesitylene inhibition with $CpZrBz_2/ZrS$ as the catalyst us shown in FIG. 3E).

Figure 4:
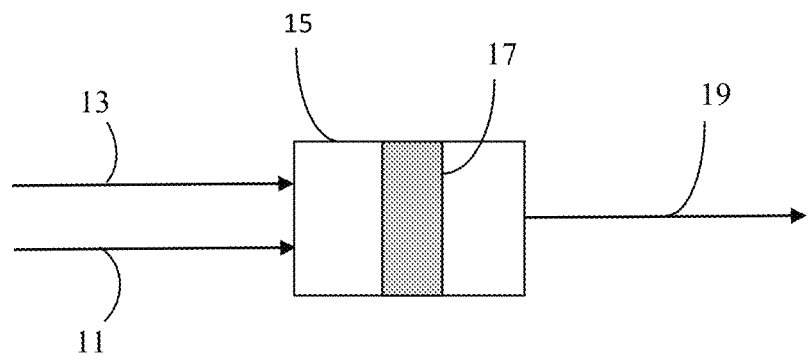

FIG. 4 is a schematic illustration of a system for reducing the amount of benzene in a gasoline product in accordance with an exemplary embodiment.

DETAILED DESCRIPTION

The following detailed description is merely exemplary in nature and is not intended to limit the various embodiments or the application and uses thereof.

Furthermore, there is no intention to be bound by any theory presented in the preceding background or the following detailed description.

Figure 1:
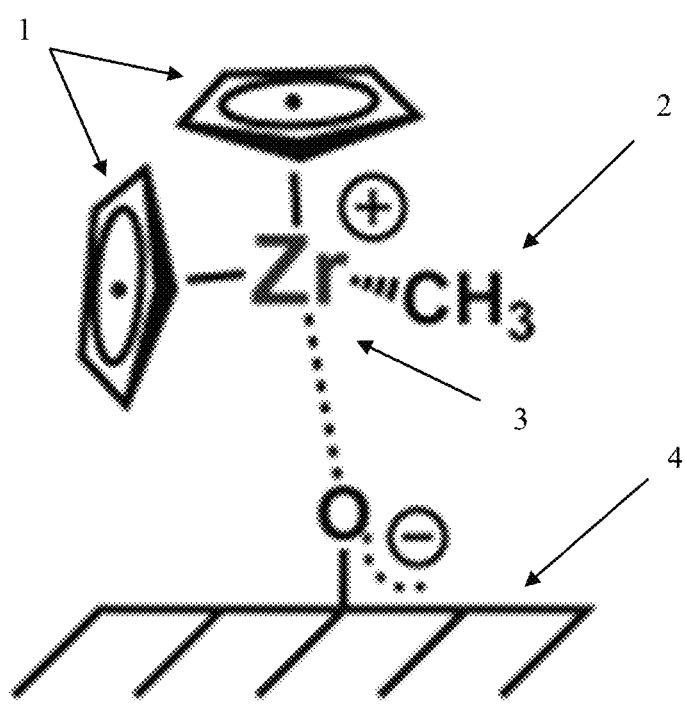
FIG. 1 is an illustration of a chemical structure of a chemisorbed $Cp_2ZrMe/ZrS$ on highly Brønsted acidic sulfated metal oxide according to an exemplary embodiment.

Various embodiments described herein are directed to methods for selectively hydrogenating benzene with supported organo-zirconium catalysts. Single-site supported catalysts have attracted interest from both academic and industrial researchers due to their uniqueness over both traditional heterogeneous and homogenous catalysts. For example, supported catalysts on super Brønsted acidic surfaces have been reported to have high reactivity towards olefin polymerization, and benzene and olefin hydrogenation. The chemical structure of one such supported catalyst ($Cp_2ZrMe$ on highly Brønsted acidic sulfated metal oxide) is seen in FIG. 1. In the depicted catalyst, the Cp ligands are seen as cyclopentadienyl ligands 1, Zr is a cationic zirconium metallic catalytic center 3 and the Me ligand is shown as the methyl (—$CH_3$) ligand 2. The organo-zirconium catalyst is attached to a highly Brønsted acidic sulfated metal oxide surface 4.

To synthesize these catalytically active organo-zirconium species, a zirconium organometallic compound with 4 ligands is contacted with a highly Brønsted acidic sulfated metal oxide. The contacting may be carried out via any of the known processes in the art including contacting a solution of the organometallic with the sulfated metal oxide followed by evaporating the solvent after a period of contact, subliming the organometallic into a space containing the sulfated metal oxide followed by evacuation of excess organometallic, or physical contact of the organometallic and the sulfated metal oxide, usually at a slightly elevated temperature such as about 66° C. Without wishing to be bound by theory, in the supporting process, one alkyl ligand reacts with the proton from the highly Brønsted acidic surface, giving an alkane and the supported cationic organo-zirconium catalyst, now with only 3 additional ligands. Solid state $^{13}C$ NMR may be used to determine that a cationic organo-zirconium catalyst has been formed by determining the chemical shift of the C in the ligand bound to Zr; examples of the use of this technique may be found in Ahn, et. al. *Organometallics*, 2002, 21, 1788-1806.

However, supported organometallic catalysts on super Brønsted acidic surfaces have not been known to be used to selectively hydrogenate benzene in the presence of other arenes (and in particular toluene). As used herein, the selectivity of a catalyst refers to a catalyst's ability to preferentially hydrogenate one arene in the presence of one or more other arenes. Selectivity is not intended to indicate that a catalyst is able to exclusively hydrogenate one arene in the presence of one or more other arenes. Rather, selectivity may occur as a matter of degree; that is, one or more arenes in a mixture may undergo hydrogenation in the presence a catalyst, and the catalyst is selective if any one arene exhibits a greater degree of reactivity relative to other arenes in the mixture. For example, in some embodiments benzene catalytic hydrogenation in the presence of one or more other arenes may be at least 10%, 25%, 50%, 100%, or more effective than catalytic hydrogenation of one or more, including all, other arenes in the mixture.

In this regard, the effectiveness of a catalyst for a particular arene is a relative measure that may be assessed by considering the amount of an arene at a given concentration in a reaction mixture that is hydrogenated by the catalyst in a given amount of time. So, if a catalyst is 50% more effective for pure benzene than pure toluene, 50% more benzene than toluene will be hydrogenated if the pure arenes are contacted with hydrogen and the catalyst under identical reaction conditions for the same amount of time. Likewise, if a catalyst is 50% more effective for benzene than toluene given a 1:1 mixture of benzene and toluene, 50% more benzene than toluene will be hydrogenated if the mixture of benzene and toluene is contacted with hydrogen and the catalyst under appropriate reaction conditions.

It has been determined that increasingly acidic inorganic oxides yield stronger surface electrophiles and thus better benzene hydrogenation reactivity. Further, investigations of the effect of different organometallic catalysts on the same support reveal that Zr-based organometallic compounds produce more active catalysts as compared to organometallic compounds based on Ti, Hf or Ta. Thus, in some embodiments, methods are provided which use organometallic catalysts based on an organo-zirconium catalyst for the selective hydrogenation of benzene.

Zr-based catalysts display reactivity differences between hydrogenation of pure benzene and pure toluene such that the catalysts are significantly more effective at hydrogenation of pure benzene than hydrogenation of pure toluene. However, it has also been found that the effectiveness of these catalysts for hydrogenation of benzene is significantly reduced when the reaction is attempted in a complex mixture of benzene in the presence of other arenes (for example, toluene). In other words, benzene reactivity is inhibited when selective benzene hydrogenation is attempted from mixtures of benzene in the presence of other arenes due to interference by the other arenes (e.g., toluene, ethylbenzene, xylenes, mesitylene, etc.).

Figure 2:
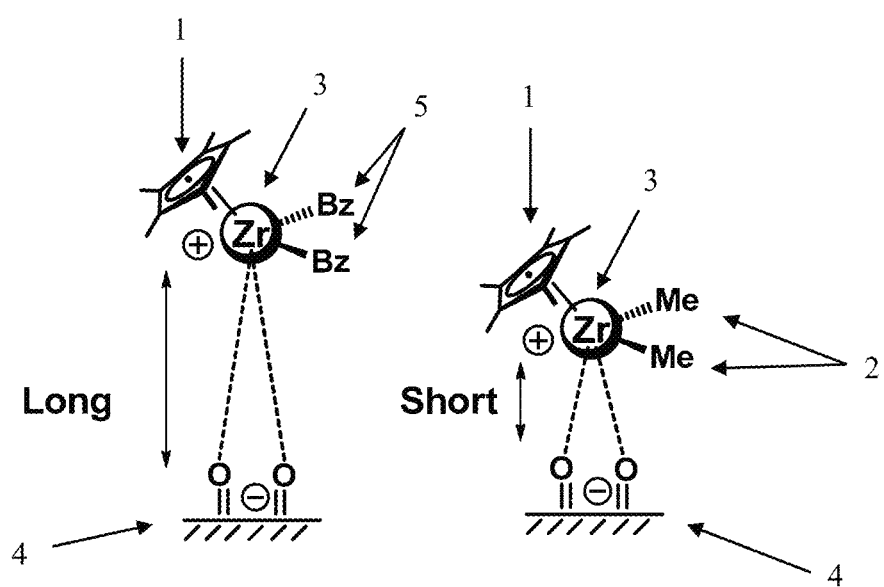
FIG. 2 is an illustration of the effect of the size of ligands on the catalytic centers of two exemplary chemisorbed organometallic species on a highly Brønsted acidic sulfated metal oxide ($Cp*ZrBz_2/ZrS$ and $Cp*ZrMe_2/ZrS$) according to two exemplary embodiments.

The organometallic catalysts used in the methods herein contain a metal atom at the catalytic center with multiple ligand groups attached thereto. Without wishing to be bound by theory, it is believed that the size of the ligand groups attached to the metallic catalytic center affects catalytic behavior in the supported catalysts. Specifically, the ligands define the space surrounding the catalytic center that is available to an arene while undergoing hydrogenation by affecting the distance between catalytic center and the surface of the support. This is illustrated in FIG. 2, where chemical structures of two different supported organo-zirconium catalysts (Cp*ZrBz$_2$/ZrS and Cp*ZrMe$_2$/ZrS) are compared. The two species shown in FIG. 2 are similar, with each having a Zr atom 3 at the catalytic center with a Cp* ligand 1 (where Cp* is a substituted or unsubstituted cyclopentadienyl, a substituted or unsubstituted cyclopentadienyl radical, or a fused cyclopentadienyl radical, where in some embodiments, embodiments a substituted cyclopendadienyl or cyclopentadienyl radical may be substituted with 1 to 5 alkyl or aryl groups, such as C1-C6 for alkyl groups or phenyl and benzyl for aryl groups), and each is adsorbed on a ZrS support surface 4. However, it can be seen that the size of the two other ligand groups on the Zr catalytic center 3 (i.e., methyl ligand groups (Me) 2 and benzyl ligand groups (Bz) 5) affect the position of the Zr catalytic center 3 relative to the support surface 4, with the smaller methyl ligand groups 2 providing a shorter distance between the Zr support surface 4 and the Zr catalytic center 3. Density functional theory (DFT) calculations predict the Zr catalytic center 3 with the smaller methyl ligand groups 2 is 2.24-2.36 Å from the Zr support surface 4. This same distance was determined experimentally by EXAFS to be 2.37±0.02 Å. In contrast, DFT calculations predict the Zr catalytic center 3 with the larger benzyl ligand groups 5 is 2.29-2.40 Å. Thus, in some embodiments, the distance between the catalytic center 3 and the Zr support surface 4 is greater than about 2.37 Å, such as greater than or equal to about 2.40 Å. The greater separation between the Zr catalytic center 3 and the Zr support surface 4 provided by larger ligand groups results in less steric hindrance at the Zr catalytic center 3, facilitating access by larger arenes.

This means that increasing the size of the ligands on the catalytic center generally increases the effectiveness of the organometallic catalyst for arenes larger than benzene. That is, that less steric hindrance at the catalytic center increases the amounts of the larger arenes that are hydrogenated from a reaction mixture in a given time. As selectivity for benzene requires the preferential hydrogenation of benzene relative to other arenes in the reaction mixture, it would be expected that increasing the catalytic effectiveness for larger arenes would reduce selectivity for benzene in a complex arene mixture. Surprisingly, however, it has been determined that this is not the case.

Rather, increasing the size of the ligand groups in the organometallic catalyst (and increasing the effectiveness of the catalyst for larger arenes) actually leads to improved selective benzene hydrogenation from a mixture of arenes. Again, without wishing to be bound by theory, it is believed that the inhibitory effect on benzene hydrogenation by larger arenes is the result of low catalytic turnover of the larger arenes in the more sterically hindered catalysts. With smaller ligand groups, once the catalytic center is occupied by a larger arene, the catalytic site remains occupied for a relatively long period of time, blocking benzene from accessing the site. Increasing the ligand group size appears to increase the catalytic site turnover for the larger arenes. A higher turnover rate reduces the inhibitory effect that larger arenes have on benzene hydrogenation, unexpectedly providing increased catalytic selectivity for benzene hydrogenation from a complex mixture.

To put it another way, supported organo-zirconium catalysts with ligands selected to improve toluene and/or other large arene hydrogenation would be expected to exhibit decreased benzene selectivity from a complex arene mixture due to their increased catalytic potential for larger arenes in the mixture. However, the observed catalytic behavior is opposite. Rather, supported organo-zirconium catalysts with ligands selected to improve toluene and/or other large arene hydrogenation exhibit increased selectivity of benzene hydrogenation over hydrogenation of other, larger arenes from a complex mixture.

As such, it has been found that some, but not all, supported organometallic catalysts on super Brønsted acidic surfaces exhibit high benzene hydrogenation reactivity with improved selectivity of benzene hydrogenation over other arene (e.g., toluene) hydrogenation at mild conditions. Certain reactions involving a single substrate are often assumed to follow Michaelis-Menten kinetics, without regard to the model's underlying assumptions. Michaelis-Menten theory can also be used to quantify inhibition according to the following kinetics equation (1), in which $V_{max}$ is the reaction rate without inhibitor, $V_0$ is reaction rate with inhibitor, [S] is the substrate concentration, [I] is the inhibitor concentration, $K_m$ is the Michaelis-Menten constant (equation (2)), and $K_i$ is the inhibitor dissociation constant.

$$V_0 = \frac{d[P]}{dt} = \frac{V_{max}[S]}{K_m + [S]} \quad (1)$$

$$K_m = \frac{1 + [I]}{K_i} \quad (2)$$

Based on the Michaelis-Menten equation (1), the Michaelis-Menten constant ($K_m$) is the substrate concentration at which the reaction rate is half of $V_{max}$. Larger $K_m$ or smaller $K_i$ implies an increased inhibition effect.

In some embodiments, the supported organometallic catalysts used in methods described herein exhibit selective hydrogenation of benzene in the presence of another arene with a Michaelis-Menten constant ($K_m$) of less than 1000, such as less than 500, such as less than 100. In some embodiments, the supported organometallic catalysts used in methods described herein exhibit selective hydrogenation of benzene in the presence of another arene with an inhibitor dissociation constant ($K_i$) greater than about $1 \times 10^{-3}$, such as greater than about $1 \times 10^{-2}$. In some embodiments, the supported organometallic catalysts used in methods described herein have a turnover frequency (TOF) of benzene in the presence of another arene of greater than about 50, such as greater than about 100, such as greater than about 200. In some of these embodiments, the another arene may be selected from the group consisting of toluene, ethylbenzene, xylenes, mesitylene, A9 aromatics and A10 aromatics.

Described herein are methods for the selective hydrogenation of benzene in the presence of one or more other arenes (and in some particular embodiments toluene) which use a supported organometallic catalyst. In some embodiments the supported organometallic catalyst is an organo-zirconium catalyst attached to a support. In some embodiments, the supported organo-zirconium catalyst is a supported version of an unsupported organo-zirconium catalyst with the general formula of $Cp^\#_c ZrR_r$, where $Cp^\#$ indicates a cyclopentadienyl ligand such as cyclopentadienyl (Cp), pentamethylcyclopentadienyl (Cp*), a cyclopentadienyl radical substituted with alkyl or trimethylsilyl groups such as 1,2-dimethylcyclopentadienyl (Cp"), or a fused cyclopentadienyl radical; c is from 0 to 2; Zr is zirconium; R is an alkyl or aromatic ligand selected from the group consisting of methyl or substituted methyl (Me), benzyl or substituted benzyl (Bz), phenyl or substituted phenyl (Ph), 2,2-dimethylpropyl (also known as neopentyl, Np) or substituted 2,2-dimethylpropyl, trimethylsilylmethyl (also known as neosilyl, Ns) or substituted trimethylsilymethyl, and 2,2-dimethylethylbenzyl (also known as neophyl, Nph) or substituted 2,2-dimethylethylbenzyl; and r is determined by the equation r=4−c. In some specific embodiments, the supported organo-zirconium catalyst is a supported version of an unsupported organo-zirconium catalyst selected from the group consisting of $Cp*ZrMe_3$, $Cp*ZrBz_3$, $Cp*ZrPh_3$, $Cp_2ZrMe_2$, and $ZrBz_4$. In an exemplary embodiment, the supported organo-zirconium catalyst is a supported version of the unsupported organo-zirconium catalyst $Cp*ZrBz_3$.

In some embodiments, the organometallic catalytic materials are adsorbed on a support material comprising a super Brønsted acidic surface (SBAS). Discussion of super Brønsted acidic surfaces can be found in the art, e.g., in Ahn, et. al. *Organometallics*, 2002, 21, 1788-1806. In some embodiments, the SBAS comprises a Brønsted acidic sulfated metal oxide support selected from the group consisting of sulfated alumina (AlS), sulfated zirconia (ZrS), sulfated titania (TiS), sulfated hafnia (HlS), sulfated iron oxide (FeS), sulfated tin oxide (TnS), tungstated zirconia (ZrW), and combinations thereof. In some embodiments, the SBAS comprises sulfated alumina (AlS), sulfated zirconia (ZrS) or tungstated zirconia (ZrW). In some embodiments, the SBAS comprises sulfated zirconia (ZrS). Thus, in some embodiments, embodiments, the supported organo-zirconium catalyst has the general formula of $Cp^{\#}_c ZrR_r/SBAS$, where $Cp^{\#}_c ZrR_r$ is as defined above, except r is determined by the equation r=3−c; and SBAS is a super Brønsted acidic surface (SBAS). In some embodiments, the supported organometallic catalysts are selected from the group consisting of $Cp*ZrMe_2/ZrS$, $ZrBz_3/ZrS$, $Cp*ZrPh_2/ZrS$, and $Cp*ZrBz_2/ZrS$.

In some embodiments, the methods described herein may be used to reduce the amount of benzene in a refinery stream. As used herein, a refinery stream may be any process or effluent stream generated during reforming or other processing of crude oil derived streams. In particular, a refinery stream may comprise a process or effluent stream generated in the treatment or preparation of a petroleum fuel, such as gasoline. In some embodiments, the amount of benzene in a refinery stream may be selectively reduced via catalytic hydrogenation with the supported organometallic catalysts to produce a gasoline product with reduced benzene content.

In some embodiments, a reaction stream (e.g., refinery stream) may comprise benzene in the presence of one or more additional arenes. In some embodiments, the one or more additional arenes comprise one or more selected from the group consisting of toluene, ethylbenzene, xylenes, mesitylene, A9 aromatics and A10 aromatics. As used herein, xylenes may include any or all of the xylene isomers ortho-xylene, meta-xylene and para-xylene; A9 aromatics may include any or all aromatic molecules containing 9 carbon atoms. Mesitylene is a specific A9 aromatic as are any of the methylethylbenzene isomers. A10 aromatics may include any or all aromatic molecules containing 10 carbon atoms. The isomers of diethylbenzene are specific examples of A10 aromatics. In some embodiments, the reaction stream (e.g., refinery stream) comprises about 1 to about 10 wt. % benzene, such as about 5 to 10 wt. % benzene. In some embodiments, the reaction stream (e.g., refinery stream) comprises about 15 to about 30 wt. % toluene, such as about 20-25 wt. % toluene. In some embodiments, the reaction stream (e.g., refinery stream) comprises about 40 to about 55 wt. % arenes. In these embodiments, the reaction stream may comprise about 1 to about 10 wt. % benzene (such as about 5 to 10 wt. % benzene), about 15 to about 30 wt. % toluene (such as about 20-25 wt. % toluene), and the remainder of the arene content (if any) being higher molecular weight arenes.

In some embodiments, selective hydrogenation of benzene is evidenced by a ratio of benzene to another arene in a method effluent being lower than a ratio of benzene to the other arene in the reaction stream (e.g., refinery stream). In some embodiments the other arene is toluene, and a ratio of benzene to toluene in a method effluent is lower than a ratio of benzene to toluene in the reaction stream (e.g., refinery stream).

Also described herein are systems and methods for reducing benzene in a gasoline product. The following exemplary systems are described with reference to FIG. 4. Exemplary systems include a reaction vessel 15 configured to contain a catalytically active organo-zirconium species on a sulfated zirconia support 17. The reaction vessel 15 is configured to receive a gasoline refinery stream 11 and hydrogen gas 13. In some embodiments, the gasoline refinery stream contains benzene, and typically contains a plurality of arene compounds, including toluene. The reaction vessel 15 is configured to contact the gasoline refinery stream 11 and hydrogen gas 13 with a supported organo-zirconium catalyst 17 under reaction conditions effective to hydrogenate benzene in the refinery stream and produce a gasoline effluent 19. As a result of contacting the catalyst in the presence of hydrogen, benzene is selectively hydrogenated relative to toluene such that a ratio of benzene to toluene in the gasoline effluent 19 is lower than a ratio of benzene to toluene in the gasoline refinery stream 11.

Methods for reducing benzene in a gasoline product include contacting a gasoline refinery stream with hydrogen in the presence of a supported organo-zirconium catalyst under reaction conditions effective to hydrogenate benzene in the gasoline refinery stream to produce a gasoline refinery effluent. In some embodiments, the gasoline refinery stream includes benzene and toluene, and the supported organo-zirconium catalyst includes a catalytically active organo-zirconium species and a sulfated zirconium support. In these methods, benzene is selectively hydrogenated relative to toluene such that a ratio of benzene to toluene in the gasoline refinery effluent is lower than a ratio of benzene to toluene in the gasoline refinery stream. In some embodiments, methods for reducing benzene in a gasoline product may be conducted on the systems described above.

The methods and systems described herein accomplish selective benzene hydrogenation under generally mild reaction conditions. The particulars of the reaction conditions may vary somewhat depending on the particular composition of the reaction stream and the physical parameters of the reaction system. Determination of suitable reaction conditions (including reaction stream flow rate, hydrogen flow rate, input temperature, catalyst temperature, etc.) may be determined by one of skill in the art. In some embodiments, these conditions may include a temperature of from about room temperature to about 250° C., a pressure of from about 1 atm to about 20 atm and a hydrogen:total arene ratio of from about 0.1 to about 100.

Those having skill in the art, with the knowledge gained from the present disclosure, will recognize that various changes could be made in the methods described herein without departing from the scope of the present invention. Mechanisms used to explain theoretical or observed phenomena or results, shall be interpreted as illustrative only and not limiting in any way the scope of the appended claims.

The following examples include representative methods of selective benzene hydrogenation in the presence of other arenes, including toluene. These examples are not to be construed as limiting as other equivalent embodiments will be apparent in view of the present disclosure and appended claims.

EXAMPLES

Arene Hydrogenation Experiments

Unless otherwise noted, the catalytic hydrogenation studies for supported catalysts described in the Examples were performed according to the following protocol. A glass reaction vessel with Morton-type indentations was used as reaction vessel. In a typical experiment, the reaction vessel was dried under high vacuum ($5 \times 10^{-7}$ Torr) for >1 h prior to experimentation. In a typical reaction, the reaction chamber was charged with 50 mg of supported catalyst and 1 mL substrates (pure or mixed arenes) in a glovebox. The sealed vessel was then transferred to the high vacuum line, evacuated and filled with $H_2$ (1.0 atm) at −78° C. The mixture was then warmed to 25° C. and stirred rapidly at 25° C. for 1 hour. After the reaction, the product was analyzed by GC/MS and $^1$H NMR.

Example 1

Studies of arene hydrogenation with various Ti, Hf, Zr, Ta catalysts supported by several acidic inorganic oxides were conducted. To examine the effect of various acidic inorganic oxide supports on catalytic behavior, a series of supported catalysts were synthesized by impregnation of Cp*ZrMe$_3$ on sulfated alumina (AlS), sulfated zirconia (ZrS) and tungstated zirconia (ZrW).

AlS, ZrS and ZrW were synthesized via literature procedures. Estimated acid strengths of these materials have been previously reported in the literature, for example at Arata, K, *Preparation of superacidic metal oxides and their catalytic action*, Wiley-VCH Verlag GmbH & Co. KGaA: 2009; pp 665-704.

Determination of benzene hydrogenation reactivity of Cp*ZrMe$_3$ supported on AlS, ZrS and ZrW supports was carried out at 25° C. under constant 1 atm $H_2$ in a slurry reactor with fast stirring (>5000 rpm), so as to minimize the influence of $H_2$ mass transfer effects. In typical reaction, 50 mg of supported catalyst and 1 mL of substrate were employed. $^1$H NMR and GC/MS were used to monitor the reactions. Cyclohexane was the only product of hydrogenation of benzene; no partially hydrogenated products, such as cyclohexene or cyclohexadiene, were observed. The results for benzene hydrogenation reactivity of Cp*ZrMe$_3$ supported on AlS, ZrS and ZrW are summarized in Table 1.

TABLE 1

Benzene hydrogenation with Cp*ZrMe$_3$ on various supported inorganic oxide supports

| Entry | Acids | Highest acid strength ($H_0$ value)[a] | Benzene hydrogenation reactivity ((mol benzene)(mol Zr)$^{-1}$ h$^{-1}$) |
|---|---|---|---|
| 1 | AlS | −14.6 | 120 |
| 2 | ZrS | −16.1 | 1200 |
| 3 | ZrW | −14.6 | 100 |

[a]Acid strengths of solid acids listed in this table are from Arata, K, *Preparation of superacidic metal oxides and their catalytic action*, Wiley-VCH Verlag GmbH & Co. KGaA: 2009; pp 665-704

As seen in Table 1, ZrS-supported catalysts exhibited a benzene hydrogenation reactivity approximately an order of magnitude greater than that exhibited by AlS and ZrW-supported catalysts.

With the same supporting organometallic species, the relative benzene hydrogenation reactivity falls in the order Cp*ZrMe$_3$/ZrS>>Cp*ZrMe$_3$/AlS>Cp*ZrMe$_3$/ZrW. The trend parallels the decrease in acidity of ZrS>>AlS≈ZrW, suggesting that more acidic inorganic oxides yield stronger surface electrophiles and therefore increased benzene hydrogenation reactivity.

Example 2

To examine the effect of the organometallic species on catalytic behavior of arene hydrogenation, a series of supported catalysts were synthesized by impregnation of Cp*MMe$_3$ (M=Zr, Ti, Hf), MBz$_4$ (M=Zr, Ti, Hf), Cp*TaMe$_4$, ($^t$BuCH$_2$)$_3$Ta(CH$^t$Bu), and Cp*ZrR$_3$(R=Ph, Bz) on ZrS as the support material. ZrS was chosen for these investigations as it was shown in Example 1 to yield the most active supported catalysts.

Benzene hydrogenation reactivity of the various organometallic species supported on ZrS was measured using the reaction protocol described above. It was shown that organometallic catalytic species with Hf, Ti, or Ta displayed much lower benzene activity compared to similar Zr-based organometallic catalytic species.

Toluene hydrogenation was also carried out under 25° C. and 1 atm $H_2$ in a slurry reactor with same set of catalysts. As observed with benzene hydrogenation, Ti, Hf, and Ta based supported catalysts were not active for toluene hydrogenation.

The results of the benzene and toluene studies for each of the tested organometallic catalysts on a ZrS support are summarized in Table 2.

TABLE 2

Arene hydrogenation results with various supported catalysts on ZrS

| | Hydrogenation Activity ((mol arene)(mol M)$^{-1}$ h$^{-1}$) | |
|---|---|---|
| Organometallic Catalyst | Benzene | Toluene |
| Cp*ZrMe$_3$ | 1200 | ≤20 |
| ZrBz$_4$ | 450 | ≤20 |
| Cp*TiMe$_3$ | ≤20 | ≤20 |
| TiBz$_4$ | ≤20 | ≤20 |
| Cp*HfMe$_3$ | ≤20 | ≤20 |
| HfBz$_4$ | ≤20 | ≤20 |
| Cp*TaMe$_4$ | ≤20 | ≤20 |
| ($^t$BuCH$_2$)$_3$Ta(CH$^t$Bu) | ≤20 | ≤20 |

Example 3

As seen in Example 2, Zr-based supported organometallic catalytic materials displayed significant reactivity differences for pure benzene hydrogenation and pure toluene hydrogenation. A variety of Zr-based supported catalyst (Cp*ZrMe$_2$/ZrS, ZrBz$_3$/ZrS, Cp*ZrPh$_2$/ZrS, Cp*ZrBz$_2$/ZrS, Cp*ZrBz$_2$/ZrS) were then selected for further studies to assess their ability to selectively hydrogenate benzene in a mixture of benzene and toluene.

Reactions for each supported catalyst were carried out with 50 mg of supported catalysts, 1 mL of benzene, 1 mL of toluene, and a mixture of 1 ml of benzene with 1 ml of toluene under 25° C. and 1 atm H$_2$ in a slurry reactor with fast stirring. The results of these reactions are summarized in Table 3.

As shown in Table 3, Cp*ZrMe$_2$/ZrS and ZrBz$_3$/ZrS both exhibit exceptional benzene hydrogenation reactivity in pure benzene. However, in the presence of a mixture of benzene and toluene, toluene is not only a poor substrate for hydrogenation but significantly inhibits benzene hydrogenation.

To investigate the impact of steric hindrance around the catalytic center, two catalysts with larger ligands (Ph and Bz) on the catalytic center were synthesized and tested for hydrogenation of benzene alone, toluene alone, and mixtures of benzene and toluene.

Both the Ph and Bz catalysts exhibited high benzene hydrogenation reactivity and much improved toluene hydrogenation when tested for reactivity with benzene alone or with toluene alone. In the case of Cp*ZrBz$_2$/ZrS, turnover frequency of toluene hydrogenation was measured to be 340 (mol)(mol Zr)$^{-1}$ h$^{-1}$, which is about 20 times higher than the same reaction with Cp*ZrMe$_2$/ZrS.

In studies with a reaction mixture of benzene and toluene, toluene displayed a weaker inhibition effect for benzene hydrogenation by Cp*ZrBz$_2$/ZrS. This appears to result from increased toluene turnover frequencies observed for catalysts with larger ligands. For example, the turnover frequency of benzene hydrogenation from a 1:1 mixture of benzene and toluene was measured to be 500 (mol)(mol Zr)$^{-1}$ h$^{-1}$ for Cp*ZrBz$_2$/ZrS, with about 2:1 selectivity for benzene over toluene.

TABLE 3

Comparative arene hydrogenation results of Zr supported catalysts on ZrS

| Organometallic Catalyst | Hydrogenation Activity ((mol arene)(mol M)$^{-1}$ h$^{-1}$) | | |
|---|---|---|---|
| | Benzene Alone | Toluene Alone | Benzene/Toluene Mix |
| Cp*ZrMe$_2$/ZrS | 1200 | ≤20 | 50/≤20 |
| ZrBz$_3$/ZrS | 450 | ≤20 | 50/≤20 |
| Cp*ZrPh$_2$/ZrS | 700 | 110 | 105/80 |
| Cp*ZrBz$_2$/ZrS | 850 | 340 | 500/250 |

Example 4

Cp*ZrBz$_2$/ZrS was then tested for selective benzene hydrogenation in the presence of other substituted arenes. The results are presented in Table 4. The turnover frequency of benzene hydrogenation from a 1:1 mixture of benzene and ethylbenzene was measured to be 490 (mol)(mol Zr)$^{-1}$ h$^{-1}$, with about 6:1 selectivity for benzene over ethylbenzene. While in the presence of mesitylene, only benzene hydrogenation was observed with a turnover frequency (TOF) around 230 (mol)(mol Zr)$^{-1}$ h$^{-1}$. However, pyridine and thiophene completely inhibited catalytic behavior, as Cp*ZrBz$_2$/ZrS displayed no hydrogenation reactivity towards benzene in the presence of pyridine or thiophene.

TABLE 4

Selective benzene hydrogenation by Cp*ZrBz$_2$/ZrS in the presence of other arenes

| Organometallic Catalyst | Hydrogenation Activity ((mol benzene)(mol M)$^{-1}$ h$^{-1}$) | | | |
|---|---|---|---|---|
| | Substrate A (Benzene) | | Substrate B | |
| Entry | Volume | TOF | Substrate | Volume | TOF |
| 1 | 1 mL | 500 | Toluene | 1 mL | 250 |
| 2 | 1 mL | 490 | Ethylbenzene | 1 mL | 80 |
| 3 | 1 mL | 230 | Mesitylene | 1 mL | 0 |
| 4 | 1 mL | 0 | Pyridine | 1 mL | 0 |
| 5 | 1 mL | 0 | Thiophene | 1 mL | 0 |

Example 5

Studies were also conducted to explore the inhibition effect of toluene or ethylbenzene on the benzene hydrogenation with ZrS supported Zr-based organometallic catalysts. Kinetics of the inhibition effects were modeled according to Michaelis-Menten theory using the Michaelis-Menten kinetic equation (1) described above for the effect of toluene, ethylbenzene or mesitylene on benzene hydrogenation with Cp*ZrBz$_2$/ZrS, Cp*ZrMe$_2$/ZrS or ZrBz$_3$/ZrS as the catalyst.

The results of inhibition effect calculations, including the Michaelis-Menten constant ($K_m$) and inhibitor dissociation constant ($K_i$) for each investigated pair, are provided in Table 5. Again, larger $K_m$ or smaller $K_i$ implies an increased inhibition effect.

TABLE 5

Competitive inhibition of different arenes on benzene hydrogenation with various supported catalysts on ZrS

| Entry | Inhibitor | Catalyst | $K_m$ | $K_i$ |
|---|---|---|---|---|
| 1 | Toluene | Cp*ZrMe$_2$/ZrS | 1266 | 1.58 × 10$^{-3}$ |
| 2 | Toluene | ZrBz$_3$/ZrS | 186 | 1.07 × 10$^{-2}$ |
| 3 | Toluene | Cp*ZrBz$_2$/ZrS | 1.08 | 1.85 |
| 4 | Ethylbenzene | Cp*ZrBz$_2$/ZrS | 1.34 | 1.49 |
| 5 | Mesitylene | Cp*ZrBz$_2$/ZrS | 1.66 | 1.20 |

With the same inhibitor toluene, the $K_i$ of the tested catalysts falls in the following order Cp*ZrBz$_2$/ZrS (1.85) >ZrBz$_3$/ZrS (1.07×10$^{-2}$)>Cp*ZrMe$_2$/ZrS (1.58×10$^{-3}$). Thus, this supported catalyst system is sensitive to small changes around the catalytic center, as changing the catalytic center ligands from methyl groups (Me) with benzyl groups (Bz) results in three orders of magnitude difference in inhibition effect.

Michaelis-Menten kinetics plots for competitive inhibition of benzene hydrogenation are shown in FIG. 3A-E. Specifically, FIG. 3A shows a competitive inhibition kinetics plot for toluene inhibition with Cp*ZrBz$_2$/ZrS as the catalyst. FIG. 3B shows a competitive inhibition kinetics plot for toluene inhibition with Cp*ZrMe$_2$/ZrS as the catalyst. FIG. 3C shows a competitive inhibition kinetics plot for toluene inhibition with ZrBz$_3$/ZrS as the catalyst. FIG. 3D shows a competitive inhibition kinetics plot for ethylbenzene inhibition with CpZrBz$_2$/ZrS as the catalyst. FIG. 3E shows a competitive inhibition kinetics plot for mesitylene inhibition with CpZrBz$_2$/ZrS as the catalyst.

The plots in FIGS. 3A-E are all similar, and surprisingly demonstrate a distinctly non-linear change in inhibition effect as the benzene:other arene ratio increases.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for selectively hydrogenating benzene with a supported organocirconium hydrogenating catalyst, the method comprising the step of:
   contacting an arene-containing reaction stream comprising benzene and one or more additional arenes with hydrogen in the presence of a supported organocirconium hydrogenating catalyst under reaction conditions effective to hydrogenate at least benzene in the arene-containing reaction stream to produce a reaction effluent having a ratio of benzene to additional arenes that is lower than the ratio of benzene to additional arenes in the arene-containing reaction stream;
   wherein the supported organocirconium hydrogenating catalyst comprises a catalytically active organocirconium species and a Brønsted acidic sulfated metal oxide support,
   wherein the catalytically active organozirconium species has the general formula $Cp^{\#}_c ZrR_r$,
   where $Cp^{\#}$ is a cyclopentadienyl ligand selected from the group consisting of cyclopentadienyl (Cp), pentamethylcyclopentadienyl (Cp*), a cyclopentadienyl radical substituted with alkyl or trimethylsilyl groups, and a fused cycolopentadienyl radical;
   c is from 0 to 2;
   R is a ligand selected from the group consisting of benzyl or substituted benzyl (Bz), phenyl or substituted phenyl (Ph), 2,2-dimethylpropyl or substituted 2,2-dimethylpropyl, trimethylsilylmethyl (neosilyl) or substituted trimethylsilymethyl, and 2,2-dimethylethylbenzyl (neophyl) or substituted 2,2-dimethylethylbenzyl;
   and r is determined the equation r=3−c, wherein benzene hydrogenation takes place with a Michaelis-Menten constant ($K_m$) of less than 500 and with a benzene TOF of greater than 100 mol (mol Zr)$^{-1}$ h$^{-1}$.

2. The method of claim 1, wherein the one or more additional arenes in the arene-containing reaction stream includes one or more arenes selected from the group consisting of toluene, ethyl benzene, xylenes, mesitylene, A9 aromatics and A10 aromatics.

3. The method of claim 1, wherein the one or more additional arenes in the arene-containing reaction stream includes toluene.

4. The method of claim 1, wherein the catalytically active organozirconium species has the formula Cp*ZrBz$_2$, where Bz is a benzyl ligand or substituted benzyl ligand, and wherein the Brønsted acidic sulfated metal oxide support is sulfated zirconia (ZrS).

5. The method of claim 1, wherein the arene-containing reaction stream comprises from about 1 to about 10 wt % benzene.

6. The method claim 1, wherein the Brønsted acidic sulfated metal oxide support is selected from the group consisting of sulfated alumina (AlS), sulfated zirconia (ZrS), sulfated titania (TiS), sulfated hafnia (HfS), sulfated iron oxide (FeS), sulfated tin oxide (TnS), tungstated zirconia (ZrW), and combinations thereof.

7. The method of claim 1, wherein the arene-containing reaction stream comprises from about 1 to about 10 wt % benzene and from about 15 to about 30 wt % toluene.

8. The method of claim 1, wherein the arene-containing reaction stream comprises from about 40 to about 55 wt % total arenes.

9. The method of claim 1, wherein the supported organozirconium hydrogenating catalyst promotes benzene catalytic hydrogenation at a rate that is at least 25% higher than the rate of catalytic hydrogenation of any other arene present in the arene-containing reaction stream.

10. A method for reducing benzene content in an arene-containing reaction stream, the method comprising the step of:
   contacting an arene-containing reaction stream comprising benzene and one or more additional arenes with hydrogen in the presence of a supported organozirconium hydrogenating catalyst under reaction conditions effectve to hydrogenate benzene in the arene-containing reaction stream to produce an effluent having a ratio of benzene to additional arenes in the effluent that is lower than the ratio of benzene to additional arenes in the arene-containing reaction stream,
   wherein the arene-containing reaction stream comprises a refinery stream, and the supported organozirconium hydrogenating catalyst comprises a catalytically active organozirconium species and a Brønsted acidic sulfated metal oxide support,
   wherein the catalytically active organozirconium species has the general formula $Cp^{\#}_c ZrR_r$.
   where $Cp^{\#}$ is a cyclopentadienyl ligand selected from the group consisting of cyclopentadienyl (Cp), pentamethylcyclopentadienyl (Cp*), a cyclopentadienyl radical substituted with alkyl or trimethylsilyl groups, and a fused cyclopentadienyl radical;
   c is from 0 to 2;
   Zr is zirconium;
   R is a ligand selected from the group comsisting of benzyl or substituted benzyl (Bz), phenyl or substituted phenyl (Ph), 2,2-dimethylpropyl or substituted 2,2-dimethylpropyl, trimethylsilylmethyl (neosilyl) or substituted trimethylsilymethyl, and 2,2-dimethylethylbenzyl (neophyl) or substituted 2,2-dimethylethylbenzyl;
   and r is determined by the equation r=3−c, wherein benzene hydrogenation takes place with a Michaelis-Menten constant ($K_m$) of less than 500 and with a benzene TOF of greater than 100 mol (mol Zr)$^{-1}$ h$^{-1}$.

11. The method of claim 10, wherein the catalytically active organozirconium species has the formula Cp*ZrBz$_2$, where Bz is a benzyl ligand or substituted benzyl ligand, and wherein the Brønsted acidic sulfated metal oxide support is sulfated zirconia (ZrS).

12. The method of claim 10, wherein the refinery stream comprises from about 1 to about 10 wt % benzene.

13. The method of claim 10, wherein the Brønsted acidic sulfated metal oxide support is selected from the group consisting of sulfated alumina (AlS), sulfated zirconia (ZrS), sulfated titania (TiS), sulfated hafnia (HfS), sulfated iron oxide (FeS), sulfated tin oxide (TnS), tungstated zirconia (ZrW), and combinations thereof.

14. The method of claim 10, wherein the arene-contianing reaction stream comprises from about 1 to about 10 wt % benzene and from about 15 to about 30 wt % toluene.

15. The method of claim 10, wherein the supported organozirconium hydrogenating catalyst promotes benzene catalytic hydrogenation at a rate that is at least 25% higher than the rate of catalytic hydrogenation of any other arene present in the arene-containing reaction stream.

16. A method for selectively hydrogenating benzene with a supported organozirconium hydrogenating catalyst, the method comprising the step of:
contacting an arene-containing reaction stream comprising benzene and one or more additional arenes with hydrogen in the presence of a supported organozirconium hydrogenating catalyst under reaction conditions effective to hydrogenate at least benzene in the arene-containing reaction stream to produce a reaction effluent having a ratio of benzene to additional arenes that is lower than the ratio of benzene to additional arenes in the arene-containing reaction stream;
wherein the supported organozirconium hydrogenating catalyst comprises a catalytically active organozirconium species and a Brønsted acidic sulfated metal oxide support,
wherein the catalytically active organozirconium species has the general formula $Cp^*ZrR_2$.
where $Cp^*$ is pentamethylcyclopentadienyl and R is a ligand selected from the group consisting of benzyl or substituted benzyl (Bz); and
wherein the supported organozirconium hydrogenating catalyst promotes benzene catalytic hydrogenation at a rate that is at least 25% higher than the rate of catalytic hydrogenation of any other arene present in the arene-contianing reaction stream.

17. The method of claim 16, wherein the Brønsted acidic sulfated metal oxide support is selected from the group consisting of sulfated alumina (AlS), sulfated zirconia (ZrS), sulfated titania (TiS), sulfated hafnia (HfS), sulfated iron oxide (FeS), sulfated tin oxide (TnS), tungstated zirconia (ZrW), and combinations thereof.

18. The method of claim 16, wherein the arene-containing reaction stream comprises from about 1 to about 10 wt % benzene and from about 15 to about 30 wt % toluene.

19. The method of claim 16, wherein the one or more additional arenes in the arene-containing reaction stream includes one or more arenes selected from the group consisting of toluene, ethyl benzene, xylenes, mesitylene, A9 aromatics and A10 aromatics.

20. The method of claim 16, wherein benzene hydrogenation takes place with a Michaelis-Menten constant ($K_m$) of less than 500 and with a benzene TOF of greater than 100 mol (mol Zr)$^{-1}$ h$^{-1}$.

* * * * *